US012746371B2

(12) United States Patent
Osman

(10) Patent No.: US 12,746,371 B2
(45) Date of Patent: Sep. 29, 2026

(54) CATHETER PLACEMENT DEVICE FOR URETHRAL APPLICATIONS

(71) Applicant: Ali Osman, Beaumont, TX (US)

(72) Inventor: Ali Osman, Beaumont, TX (US)

( * ) Notice: Subject to any disclaimer, the term of this patent is extended or adjusted under 35 U.S.C. 154(b) by 119 days.

(21) Appl. No.: 18/944,882

(22) Filed: Nov. 12, 2024

(65) Prior Publication Data

US 2025/0065084 A1 Feb. 27, 2025

Related U.S. Application Data

(60) Division of application No. 18/488,193, filed on Oct. 17, 2023, now Pat. No. 12,168,107, which is a (Continued)

(51) Int. Cl.

| | |
|---|---|
| ***A61M 25/09*** | (2006.01) |
| ***A61B 1/00*** | (2006.01) |
| ***A61B 1/005*** | (2006.01) |
| ***A61B 1/015*** | (2006.01) |
| ***A61B 1/06*** | (2006.01) |
| ***A61B 1/307*** | (2006.01) |
| ***A61M 3/02*** | (2006.01) |
| ***A61M 25/00*** | (2006.01) |

(52) U.S. Cl.

CPC ... *A61M 25/09041* (2013.01); *A61B 1/00016* (2013.01); *A61B 1/00082* (2013.01); *A61B 1/00147* (2013.01); *A61B 1/00154* (2013.01); *A61B 1/0051* (2013.01); *A61B 1/015* (2013.01); *A61B 1/0661* (2013.01); *A61B 1/307* (2013.01); *A61M 3/0279* (2013.01); *A61M 25/0068* (2013.01); *A61M 25/0905* (2013.01); *A61M 2025/09008* (2013.01); *A61M 2205/10* (2013.01); *A61M 2210/1085* (2013.01)

(58) Field of Classification Search

CPC ............ A61B 1/00082; A61B 1/00147; A61B 1/00154; A61B 1/0051; A61B 1/0015; A61B 1/00108; A61B 1/00135; A61B 1/012; A61B 1/0125; A61B 1/018; A61B 1/051; A61B 1/052; A61B 1/0082; A61B 1/000154; A61B 1/307; A61M 25/09; A61M 25/09014; A61M 25/0905; A61M 25/10; A61M 25/0017; A61M 2025/09116

See application file for complete search history.

(56) References Cited

U.S. PATENT DOCUMENTS 4,858,810 A * 8/1989 Intlekofer .......... A61B 17/3403 24/115 M

* cited by examiner

*Primary Examiner* — Aaron B Fairchild
(74) *Attorney, Agent, or Firm* — David Colls; Berger Singerman LLP

(57) ABSTRACT

A portable hand-held medical device includes a body having a gun-type formation that includes a barrel. A guide wire device is housed in the body and is configured to advance and retract through the barrel. The guide wire device carries a bundled arrangement including a video system, an illumination system to support the video system, a fluid irrigation line, and a guide wire mechanism. The bundled arrangement is packaged as a unit in an insertion tube. The tip section of the insertion tube incorporates a camera, a light source, and a fluid irrigation port. A catheter is disposed at the end of the barrel, so that during operation the guide wire device passes through the catheter lumen. The combination guide wire device and catheter enter the urinary tract and perform a bladder evacuation process.

12 Claims, 8 Drawing Sheets

Related U.S. Application Data continuation of application No. 17/387,200, filed on Jul. 28, 2021, now Pat. No. 11,833,317.

(60) Provisional application No. 63/072,575, filed on Aug. 31, 2020.

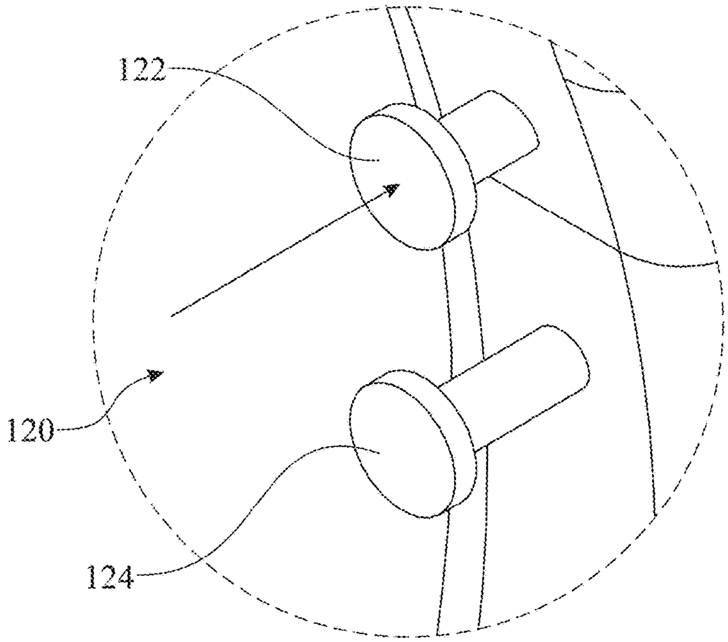
FIG. 3
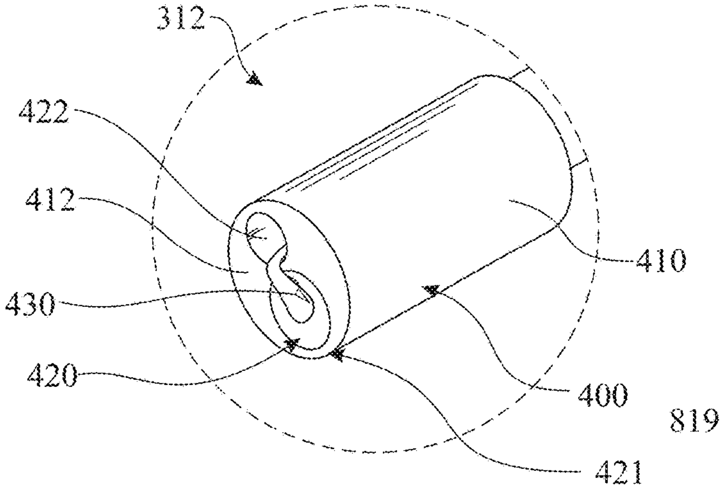
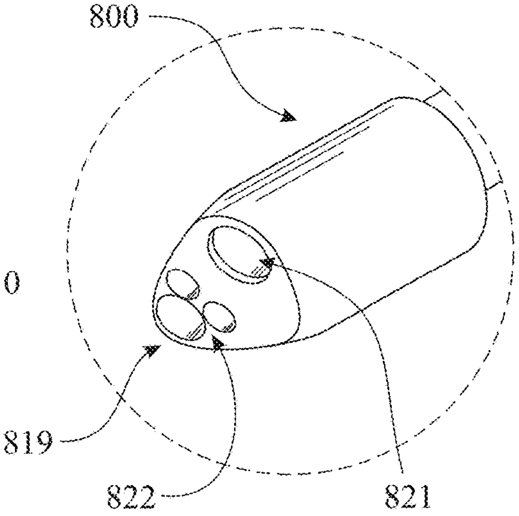
FIG. 3a
FIG. 3b

CATHETER PLACEMENT DEVICE FOR URETHRAL APPLICATIONS

CROSS-REFERENCE TO RELATED APPLICATIONS

This divisional application claims the benefit of U.S. Continuation patent application Ser. No. 18/488,193, filed on Oct. 17, 2023, U.S. Nonprovisional patent application Ser. No. 17/387,200, filed on Jul. 28, 2021, and U.S. Provisional Patent Application Ser. No. 63/072,575, filed on Aug. 31, 2020, all of which are incorporated herein in their entirety.

FIELD OF THE INVENTION

The present invention relates generally to medical instruments, and, more particularly, to a device configured to perform the placement of a urinary catheter in a urethral channel as part of a bladder evacuation procedure.

BACKGROUND OF THE INVENTION

Emergency Departments all over the world are accustomed to receiving patients with a wide variety of illnesses. Some of these cases may seem unconventional to the regular population, but they are usually routine work for the experienced physicians and other health care workers who are often exposed to such strange cases. However, a common misconception surrounding the Emergency Department involves a widespread belief that they receive extraordinary and gruesome cases daily and emergency departments are fully staffed with all sorts of medical and surgical specialists and subspecialists. This is far from the truth because the most common cases many emergency physicians deal with include chronic back pain, abdominal pain, chest pain, and headaches. Although these are far from gruesome and exciting, there may be an underlying cause for the pain that could be life threatening.

Among the cases that are regularly seen by emergency physicians is urinary retention, which occur more often in male patients. Urinary retention occurs when an individual is unable to empty their bladder of stored urine. In some cases, the patient is unable to empty their bladder, and must urinate often. In more painful and serious cases, the patient is unable to urinate, allowing the bladder to become increasingly distended as it is filled with urine but not emptied. According to an acute urinary retention study on men over a two-year period performed by Choong and Emberton, urinary retention was caused by benign prostatic hyperplasia (BHP) in 53 percent of patients. BHP is a non-malignant growth of the prostate gland. The prostate gland may reach a size where it will eventually lead to obstruction of the urethra and prevent the bladder from being emptied. Another common cause of urinary retention is by means of a urethral stricture. These strictures, or the narrowing of the urethra, can arise from injuries, previous prostate surgery, kidney stone removal, urinary catheterization, among many others. Because males have longer urethras, they are much more susceptible to strictures than females.

In order to alleviate the pain from patients who present with urinary retention feel, a urinary catheterization procedure is necessary. During this procedure, a small tube known as a urinary catheter is inserted into the patient's bladder through the urethra. The catheter allows the patient's bladder to be drained, serving as a urethra. Male catherization can be difficult, especially in patients with an enlarged prostate or urethral strictures (i.e., scarring that narrows the urethral passageway). Repeated attempts at blind catherization—without the use of catheter guidance tools—can cause pain to the patients, injury to the urethra, and potential complication requiring surgical intervention. Unfortunately, blind catherization is a commonly used technique. The techniques that employ direct visualization of the bladder are either cumbersome or most likely require the involvement of urology specialist which is not always readily available in the Emergency Department. Immediate urethral catherization and evacuation of the urine from the distended bladder brings immediate relief to the patient. Safer methods of performing this procedure, with the use of guidance tools and visualization from a camera, will prevent creation urethral false lumen—caused by repeated attempts at blind catheter placement—and avoid urethral rupture and future complication requiring surgical repair.

Accordingly, there is an established need for a urinary catheter placement device that is capable of performing immediate bladder catheterization without undue delay, avoids urethral trauma from mispositioned or misguided insertion tools, enables a wider range of medical professionals beyond urology specialists to operate the device, facilitates medical care in an outpatient setting to thereby lower healthcare costs and reduce surgical risks, and avoids the complications of blind catheterization protocols.

SUMMARY OF THE INVENTION

The present invention is directed to a portable hand-held medical device that includes a body having a gun-type formation. The body includes a barrel having a bore or lumen. A guide wire device is housed in the body and is configured to advance and retract through the barrel lumen. In alternative embodiment, the guide wire is removably attachable to the barrel of the device. The guide wire device carries a bundled arrangement including a video system, an illumination system to support the video system, a fluid irrigation line, and a guide wire mechanism. The bundled arrangement is packaged as a unit and housed in an insertion tube, which forms part of the guide wire device. The tip section of the insertion tube incorporates a camera, a light source, and a fluid irrigation port. The tip section further includes a wire bending mechanism that facilitates steering of the guide wire device. A catheter is disposed at the end of the barrel, so that during operation the guide wire device passes through the catheter lumen.

Introducing a first embodiment of the invention, the present invention consists of a portable hand-held medical device, comprising:

- an instrument including a body and a barrel extending from the body, the barrel defining a bore having a distal portion with an opening;
- a catheter having an open ended proximal portion and an open ended distal portion and defining a lumen, the proximal portion of the catheter receivable over the distal portion of the barrel bore, the distal portion of the catheter having a tip section with an axial opening in communication with the lumen;
- an inflatable balloon carried by the catheter;
- a guide wire assembly carried by the instrument and having a proximal portion and a distal portion including a tip section, the guide wire assembly configured to selectively advance and retract along at least one path of travel including at least one of the barrel bore, the catheter lumen, and locations external to the catheter via the axial opening at the tip section of the distal portion thereof;

the guide wire assembly including:

an insertion tube defining a lumen and having a proximal portion and a distal portion including a tip section, a controllable guide wire mechanism carried in the lumen of the insertion tube and capable of longitudinal movement, the guide wire mechanism including a bendable and steerable guide wire tip section, a video recording feature including a video camera disposed at the tip section of the distal portion of the insertion tube, an illumination feature including a light source disposed at the tip section of the distal portion of the insertion tube, and a controllable irrigation feature including an irrigation fluid dispensing port disposed at the tip section of the distal portion of the insertion tube;

a control mechanism integral with the instrument, the control mechanism configured to enable an operator to selectively control longitudinal movement of the guide wire mechanism and to selectively control bending movement of the guide wire tip section of the guide wire mechanism; and the control mechanism further configured to enable the operator to selectively control a fluid discharge operation of the irrigation feature.

In another aspect, the portable hand-held medical device may comprising a switch disposed on an upper region of the body of the instrument. The switch is to be electronically connected to a motor mechanism that engages the guide wire assembly. The motor mechanism, controlled by the switch, controls the motor's mechanism ability to either advance or retract the guide wire assembly through the instrument body, through the bore and lumen of the catheter and into an orifice of a patient.

In another aspect, the control mechanism may include at least one operational control member or joystick configured to articulate a movement action of the distal portion of the guide wire assembly. In one exemplary embodiment, the movement or articulation of the distal portion of the guide wire is proportional to the movement or articulation of the operational control member. The operational control member is configured to direct the longitudinal movement of the guide wire assembly and the directional movement of the tip section of the distal portion of the guide wire assembly.

In another aspect, the open ended proximal portion of the catheter is attachable to a distal portion of the barrel extending from the body of the instrument, and the open ended distal portion of the catheter may include at least one evacuation opening.

According to the first embodiment of the invention, the present invention further consists of a method of drawing urine from a patient bladder, comprising the steps of:

advancing a guide wire into the bladder cavity via the urethra;

monitoring the guide wire advancement by using video images acquired by a video camera disposed at a distal portion of the guide wire;

passing a catheter over the guide wire until the catheter traverses at least the neck of the bladder;

withdrawing the guide wire from the patient;

inflating a dilator balloon carried by the catheter to secure the catheter; and evacuating urine from the patient bladder via the secured catheter.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 3 presents an enlarged, sectional front perspective view of the trigger mechanism of the first embodiment of the urinary catheter placement device of the present invention, illustrating how the trigger selector is operated to control an irrigation feature;

FIG. 3*a* presents an enlarged, sectional front perspective view of the distal tip of the guide wire unit of the first embodiment of the urinary catheter placement device of the present invention, illustrating how the irrigation feature disclosed in FIG. 3 serves to clean the lenses of a combination camera and light source unit;

FIG. 3*b* presents an enlarged, sectional front perspective view of an alternative design for the distal tip of the guide wire unit of the first embodiment of the urinary catheter placement device of the present invention, illustration the irrigation feature, the light source and the camera source of the unit.

Like reference numerals refer to like parts throughout the several views of the drawings.

DETAILED DESCRIPTION

Figure 1:
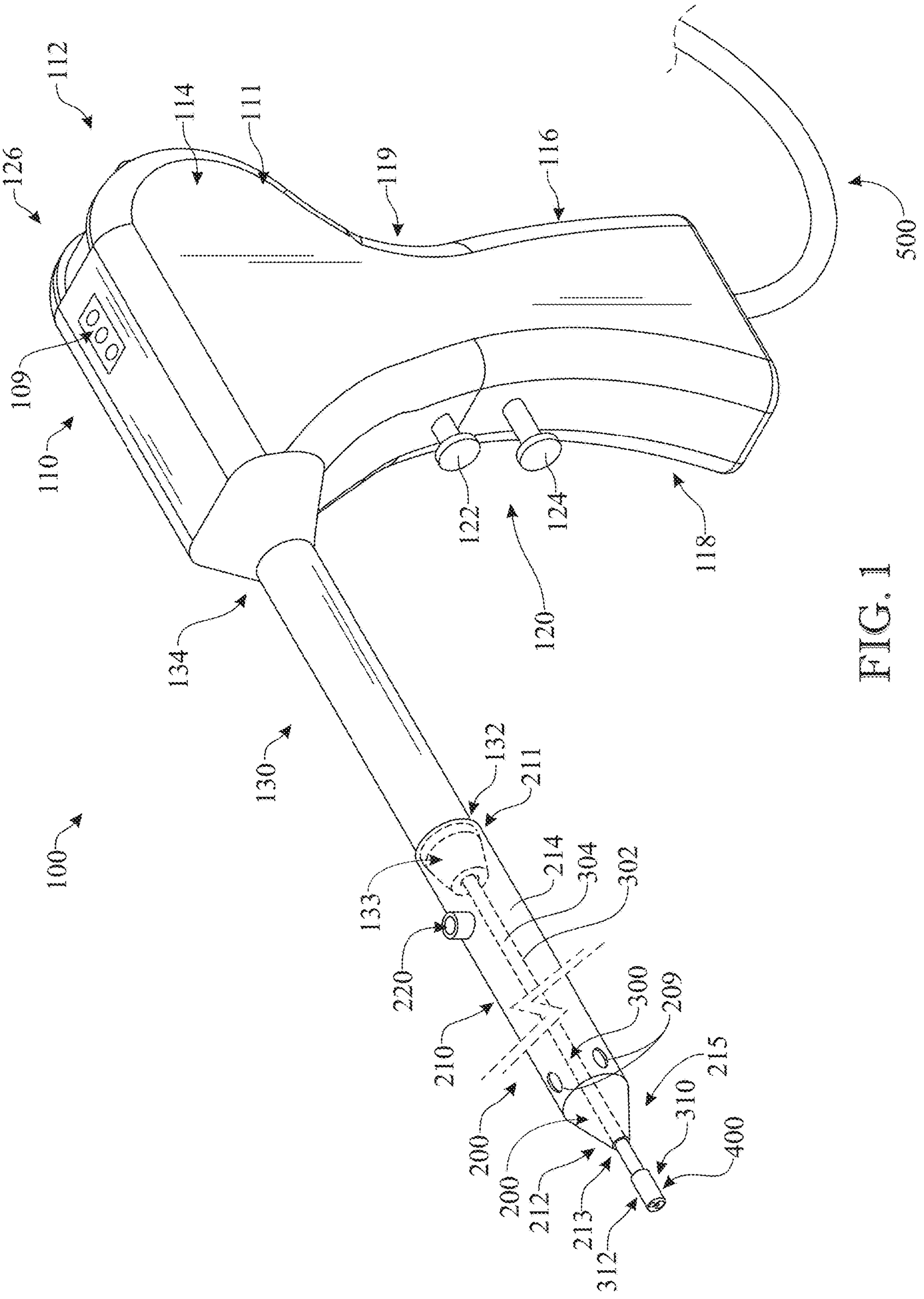
FIG. 1 presents a front, side, upper perspective view showing a first embodiment of the urinary catheter placement device of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a method and apparatus to perform a urethral catheterization and urine evacuation process, specifically in applications involving male patients. More particularly, according to one exemplary implementation, the present invention is directed to a portable hand-held medical device that includes a body having a gun-type formation. The body includes a barrel having a bore or lumen. A guide wire device, in one embodiment selectively attachable to the barrel of the device, or in an alternative embodiment housed in the body and configured to advance and retract through the barrel lumen. The guide wire device carries a bundled arrangement including a video system, an illumination system to support the video system, a fluid irrigation line, and a guide wire mechanism. The bundled arrangement is packaged as a unit and housed in an insertion tube, which forms part of the guide wire device. The tip section of the insertion tube incorporates a camera, a light source, and a fluid irrigation port. The tip section further includes a wire bending mechanism that facilitates steering and maneuvering of the guide wire device, a feature that finds use when the guide wire device is inserted into the urethra and navigated to the bladder. A catheter is disposed at the end of the barrel, so that during operation the guide wire device passes through the catheter lumen. The combination guide wire device and catheter enter the urinary tract and perform a bladder evacuation process. The camera-equipped tip section of the guide wire device enables the operator to visualize the passage of the guide wire device through the urethra on its course to the bladder, a feature that allows the user to visually monitor the progress of the guide wire device and make appropriate adjustments to the navigation.

Referring initially to FIG. 1, a hand-held, portable medical device is generally illustrated at 100, according to a first embodiment of the present invention. The medical device 100 facilitates and performs a catheter procedure, specifically a process of urethral catheterization and urine evacuation from the bladder. Generally, FIGS. 1-5 disclose structural and functional aspects of device 100, while FIGS. 6-8 disclose an application of device 100 directed to an exemplary process of placing a catheter into the urogenital structure of a male patient (namely, the bladder via full traverse of the urethra) and evacuating urine from the bladder.

As discussed further, device 100 provides various functionalities relating to the catheterization of a male patient undergoing treatment for urinary evacuation of the bladder. The device 100 houses and controls the movement of a guide wire device generally illustrated at 300. The guide wire device 300, under the direction of user control, is able to selectively advance and retract, features that allow the user to manage the navigation of guide wire device 300 as it enters the urethra and migrates to the bladder. Alternatively, the guide wire device may be selectively attached to the distal end portion of the device 100 and then navigated into the urethra. As a piloting mechanism, guide wire device 300 establishes the path for insertion and movement of a catheter generally illustrated at 200, which in operation passes over and tracks guide wire device 300. The guide wire device 300 assists the catheter 200 to insert, position, and move relative to the urethra and bladder. Specifically, in operation, catheter 200 passes over the installed guide wire device 300, starting from a position external to the patient, entering the urethral opening, traveling through the urethral tract, and finally entering the bladder via the bladder neck. Catheter 200 follows a course that tracks the guide wire device 300 until it reaches the patient's bladder, where further treatment is conducted (i.e., urinary evacuation). The guide wire device 300 is equipped at its distal tip section with a viewing and monitoring unit generally illustrated at 400. The viewing unit 400 (carried by guide wire device 300) includes a video functionality that permits the operator to visualize a live feed of the ambient environment at the distal tip of guide wire device 300. The video-equipped feature of device 100 supports direct visualization of the urethra, which assists the operator in the navigation and steering of guide wire device 300 as it travels the urethral tract, eventually traversing the neck of the bladder and entering the bladder cavity. The guide wire device 300 also carries an irrigation feature at its distal tip section to provide a cleaning functionality.

Referring more particularly to FIG. 1, the medical device 100 includes a tool or instrument body generally illustrated at 110. In one implementation, the instrument body 110 is preferably configured in the form of a gun-style configuration that includes an upper portion 112, a lower portion 116, a front side 118, and a rear side 119. The lower body portion 116 forms a grip handle that enables a user to readily hold and handle device 100 in a familiar gun-style manner, where rear side 119 receives the palm of the user and the front side 118 receives the fingers of the user (e.g., index and middle fingers), according to a conventional gun-grasping gesture. The device 100 further includes a barrel generally illustrated at 130, which projects forward in a conventional gun-type manner from a front upper section of body 110, which defines a proximal portion 134 of barrel 130. The barrel 130 defines an inner cavity, bore, or lumen. The barrel 130 includes a distal portion 132 terminating in a tip section 133 having an opening in communication with the barrel bore. The medical device 100, in various forms, can be variously considered a tool, instrument, or implement configured as a urinary catheter placement device.

The medical device 100 further includes a guide wire device or assembly 300 that is configured, in one form, as an insertion tube. In this form, guide wire device 300 includes a generally tubular body 302 defining a conduit or lumen 304. In one embodiment, the guide wire device 300 is housed within the body 110 of medical device 100 and can be controllably dispensed or fed from device 100. In particular, guide wire device 300 is configured to advance and retract through the bore or lumen of barrel 130. The lumen of barrel 130 is preferably sized relative to guide wire device 300 to stabilize the passage of guide wire device 300 and to adequately restrain or limit its non-longitudinal movement so as to support guide wire device 300 in its axial passage through barrel 130. The guide wire device 300 includes a distal portion 310 that serves as the leading point of entry when guide wire device 300 is admitted or introduced into the urinary tract of the patient (i.e., urethra). In particular, the distal portion 310 occupies the leading position when guide wire device 300 is operated in an advancing mode (and occupies the trailing position when guide wire device 300 is retracted). The process of feeding guide wire device 300 from medical device 100 (via barrel 130) involves unwinding guide wire device 300 from its stored condition as a spool or coiled reel, thereby advancing guide wire device 300 through barrel 130, where it emerges from the distal end of barrel 130 for further navigation into the urinary tract. The advanced guide wire device 300 can be returned to medical device 100 in a retraction process, which winds guide wire device 300 back into its stored coiled reel arrangement. In an alternative exemplary embodiment, the same function of the advancement and retraction of the guide wire 300 is done manually. Put differently, instead of the wire advancing through the barrel via the operation of the control mechanism 120, the wire is is manually inserted and retracted into the urinary tract.

As discussed further, guide wire device 300 incorporates and houses various operational features. One feature involves a guide wire mechanism that facilitates controlled steering of the insertion tube 302. Another feature involves a video capability at the leading end of guide wire device 300, so that images can be recorded of the immediately proximate, approaching path in front of guide wire device 300. Yet another feature involves the use of a light source that illuminates the path in front of the guide wire device 300, working in tandem with the video capability to deliver clear images. Still another feature involves the use of an irrigation mechanism to disperse cleaning fluid that helps maintain the lenses of the video and light combination free of debris.

Referring still to FIG. 1, and in further reference to FIG. 3*a*, the medical device 100 includes a viewing and monitoring unit generally illustrated at 400, which is carried and otherwise housed by guide wire device 300. In particular, viewing unit 400 is located at the tip or terminal section 312 of distal portion 310 of guide wire device 300. The viewing unit 400 forms an integral part of the tip section 312 of distal portion 310. The viewing unit 400 includes a body 410 that houses a video camera and light source combination generally illustrated at 422. This combination 422 features the ability to capture video images via the video camera. Because the viewing unit 400 operates inside the patient anatomy, it requires some type of illumination to make anything visible. To address this requirement, the light source of combination 422 operates in tandem with the video camera, illuminating the surrounding, interior environment (i.e., urethra and bladder) in the manner of a directional headlight. As shown, the video camera and light source combination 422 is preferably disposed at the front-most terminus 412 of body 410 of unit 400. Because of its location at the leading edge of guide wire device 300, the video camera feature of combination 422 is able to capture images of the urethral space in the immediate surrounding vicinity of distal portion 310, particularly in front of distal portion 310, once guide wire device 300 is inserted into the urethra (at distal portion 310) and advanced through the urethra. The light source feature of combination 422 illuminates this ambient space in front of distal portion 310, so that clear images can be captured by the video camera feature. During application of device 100, this ambient space is the interior environment of the urethra and bladder. The video camera and light source features of combination 422 enable an operator to receive instantaneous video feedback on the location and positioning of the leading edge of guide wire device 300 as it traverses through the urethra and into the bladder, providing real-time monitoring of the movement of guide wire device 300 and facilitating a safe navigation of guide wire device 300 through the urethral space and into the bladder.

In one form, the video camera and light source combination 422 is part of an integrated video monitoring system that allows the operator to view the images generated by the video camera on an external display screen. In one exemplary embodiment, the video camera and light source combination 122 may be internally connected to a connection port 109 disposed about the top portion of the body 110 of the device 100. The video camera and light source may also or exclusively include the necessary components, such as small electronic chips, to enable wireless connectivity via Bluetooth or Wi-Fi to an electronic device (not shown) that allows the operator to view the images generated by the video camera as the device makes is way through the urethra of a person. Alternatively, the electronic device can be hardwired to the medical device 100 via connection port 109. In one implementation, for example, the medical device 100 is integrated with a video display system that receives and displays the video images acquired by the video camera of viewing unit 400. For this purpose, an appropriate communication line is provided between the video camera of viewing unit 400 and an external display monitor of the video display system. For example, in one implementation, a fiber optic transmission channel extends from the video camera, passes through lumen 304 of the insertion tube 302 of guide wire device 300, and is connected to an exterior fiber optic cable 500 running from medical device 100 (FIG. 1). This external fiber optic cable is connected to the video input cable of a display monitor using any suitable adapter or coupler. Any conventional means well known to those skilled in the art can be used to configure this video link. The video signals captured by the video camera of viewing unit 400 are transmitted over this fiber optic channel that extends through lumen 304 of insertion tube 302. In another embodiment, the video camera of viewing unit and light are wirelessly connectable via Bluetooth®, internet, or any readily available wireless connection to an electronic device. For instance, the camera and light may be programmable to operate through a web application (i.e., an app), to transmit live video to the electronic device, which can be a smart phone, tablet, computer, or laptop of any kind.

Referring further to FIG. 3*a*, the housing 410 of viewing unit 400 is equipped with an irrigation line generally illustrated at 420, which includes an irrigation outlet port or orifice 421 located at the front terminal face 412 of housing

410. The irrigation port 421 serves as an orifice through which liquid 430 is discharged to facilitate cleaning of the exposed surfaces of the video camera and light source combination 422, specifically the camera lens and the light source lens. The pattern of liquid discharge 430 is such that the cleaning fluid is directed to the various lenses of viewing unit 400. In order to deliver fluid to irrigation port 421, the irrigation fluid line 420 is provided in the lumen 304 of insertion tube 302 of guide wire device 300. The proximal end of this irrigation fluid line 420 is connected to the irrigation port 421, while the distal end is connected to a source of cleaning fluid, such as a supply of saline solution. Various means can be used to form this irrigation system and provide the fluid supply. In one implementation, for example, a fluid reservoir can be stored at an interior compartment 111 of the body 110 of medical device 100, with an internal connection being made between this interior fluid reservoir and the irrigation fluid line 420 passing through lumen 304 of insertion tube 302. Alternately, the supply of cleaning fluid can be provided as an external component. For this purpose, an access port can be provided on the body 110 of medical device 100, which is internally connected to the irrigation fluid line 420 passing through lumen 304. At the appropriate time, the external source of cleaning fluid can be connected to this access port on medical device 100 to deliver fluid on request. Other suitable implementations may be possible within the knowledge of one skilled in the art. As discussed further, the dispensing of cleaning fluid (via irrigation port 421 at the distal end 310 of guide wire device 300) can be controlled by the user via activation of controls on medical device 100.

The guide wire device 300 further includes a guide wire mechanism to control the movement of insertion tube 302 and, hence, the components carried by insertion tube 302, namely, the viewing unit 400 and the irrigation line 420. The guide wire mechanism extends within and through the lumen 304 of insertion tube 302 of guide wire device 300. The guide wire mechanism extends fully to the distal terminus of insertion tube 302, namely, distal portion 310. The guide wire mechanism is preferably coextensive with insertion tube 302. This guide wire mechanism, in one form, may have a conventional construction, including, but not limited to, a solid core construction. Any suitable conventional guide wire mechanism can be used as known to those skilled in the art. Preferably, the guide wire mechanism will incorporate a tip-bending feature at distal portion 310 of guide wire device 300. For example, in a conventional manner, the guide wire mechanism will have a generally stiff body and a generally floppy bendable tip, which offers a balance between the onmi-directional steering and navigational ability offered by a supple tip and the pushability offered by the stiffer section of the wire. The ability to adjust the directionality of such a bendable guide wire tip is beneficial because it enhances the ability of the viewing unit 400 (which moves in tandem with the bendable guide wire tip) to have a wider field of vision within the urethra and bladder, features that improve the navigation of the guide wire device 300 through the small urethra diameter caused by prostate hypertrophy and strictures. The viewing unit 400, due to its location at the distal portion 310 of guide wire device 300, will maneuver about in tandem with, and in response to, the movements of the bendable guide wire tip, which preferably is capable of omni-directional travel. It will be apparent that the various properties of the guide wire design can be tailored to the specific application, as well known to those skilled in the art. These properties include, but are not limited to, pushability (the amount of force needed to advance the wire), steerability (the ability and responsiveness of the wire tip to navigate vessels), torque (the response of the wire to turning by the operator when navigating vessels), and opacity (the level of visibility under fluoroscopic imaging). Additionally, any suitable size (e.g., diameter), length, and material construction of the guide wire mechanism can be used.

The combination of components carried by insertion tube 302 of guide wire device 300 may be bundled into a single unitary package to promote case, consistency, and uniformity of movement. In such a bundled arrangement, for example, the following components are bound into a single unitary arrangement: the irrigation line 420, the fiber optic line connecting to the viewing unit 400 (i.e., the connection lines to the video camera and light source combination 422), and the guide wire mechanism, which will drive the movement of this bundled arrangement. The bundled arrangement will extend within and through the lumen 304 of insertion tube 302. The advantage of such a bundling configuration is that everything will move in tandem with, and in response to, the guide wire mechanism, which serves as the facility to steer and direct the movement of guide wire device 300. The proximal end of this bundled package (i.e., the combination of insertion tube 302 and the guide wire bundle it carries in lumen 304) is preferably loaded as a coiled reel or spool inside medical device 100, such as within an interior compartment space generally indicated at 114 (FIG. 1). This coiled reel can be selectively unwound and wound, corresponding to operations that respectively advance and retract guide wire device 300.

Referring again to FIG. 1, medical device 100 further includes a catheter 200 having a body 210 defining a lumen 214 having a proximal portion 211 and a distal portion 212. In one form, the body 210 of catheter 200 has a tubular construction. The proximal portion 211 of catheter 200 has an open end. During assembly or after preassembled, the proximal portion 211 of catheter 200 is located over the distal portion 132 of barrel 130 of device 100. In order to make this coupling, the distal portion 132 of barrel 130 is suitably formed with a tip section 133 that receives the proximal portion 211 of catheter 200 in a telescoping, overlapping, interfit engagement. In one configuration, for example, the tip section 133 has a tapered or reduced diameter profile that is sufficiently reduced in its cross-sectional profile to accommodate the placement of catheter proximal portion 211 in an outer annular relationship over the barrel tip section 133. One possible geometry of tip section 133 is frusto-conical. In this interfit relationship between catheter 200 and medical device 100 (via barrel 130), the front opening at the terminus of tip section 133 of barrel 130 is in communication lumen 304 of catheter 300. In this manner, the guide wire device 300, which is carried by device 100 and unreeled through barrel 130, can transition in its travel from barrel 130 to the lumen 304 of catheter 300 as guide wire device 300 is operationally extended or advanced. At the opposite end of catheter 200 from proximal portion 211, the distal portion 212 includes a tip section 215 having an opening generally illustrated at 213, which is in communication with the catheter lumen 304. The front opening 213 in tip section 215 is suitably dimensioned to accommodate guide wire device 300 as it moves through the catheter lumen 304 and traverses opening 213, during operational phases including both the advancement and withdrawal of guide wire device 300. The tip section 215 preferably has a reduced cross-sectional profile that terminates at a front section where opening 213 is located. This tapered profile of tip section 215 is advantageous to facilitate insertion of catheter 200 into the urethral opening and to promote case of travel through the urinary tract, since tip section 215 is the leading edge of catheter 200 during advancement and defines the point of entry. A blunt leading edge could make catheter insertion and travel more difficult. The opening at the tip section 215 of catheter 200 is appropriately sized to accommodate the movement of guide wire device 300 through it and to add a measure of stability to the passage of guide wire device 300. The tip section 215 also includes a pair of evacuation openings 209 that aid in the evacuation of urine in the event the opening where the guide wire passes becomes clogged (FIG. 1).

Figure 2:
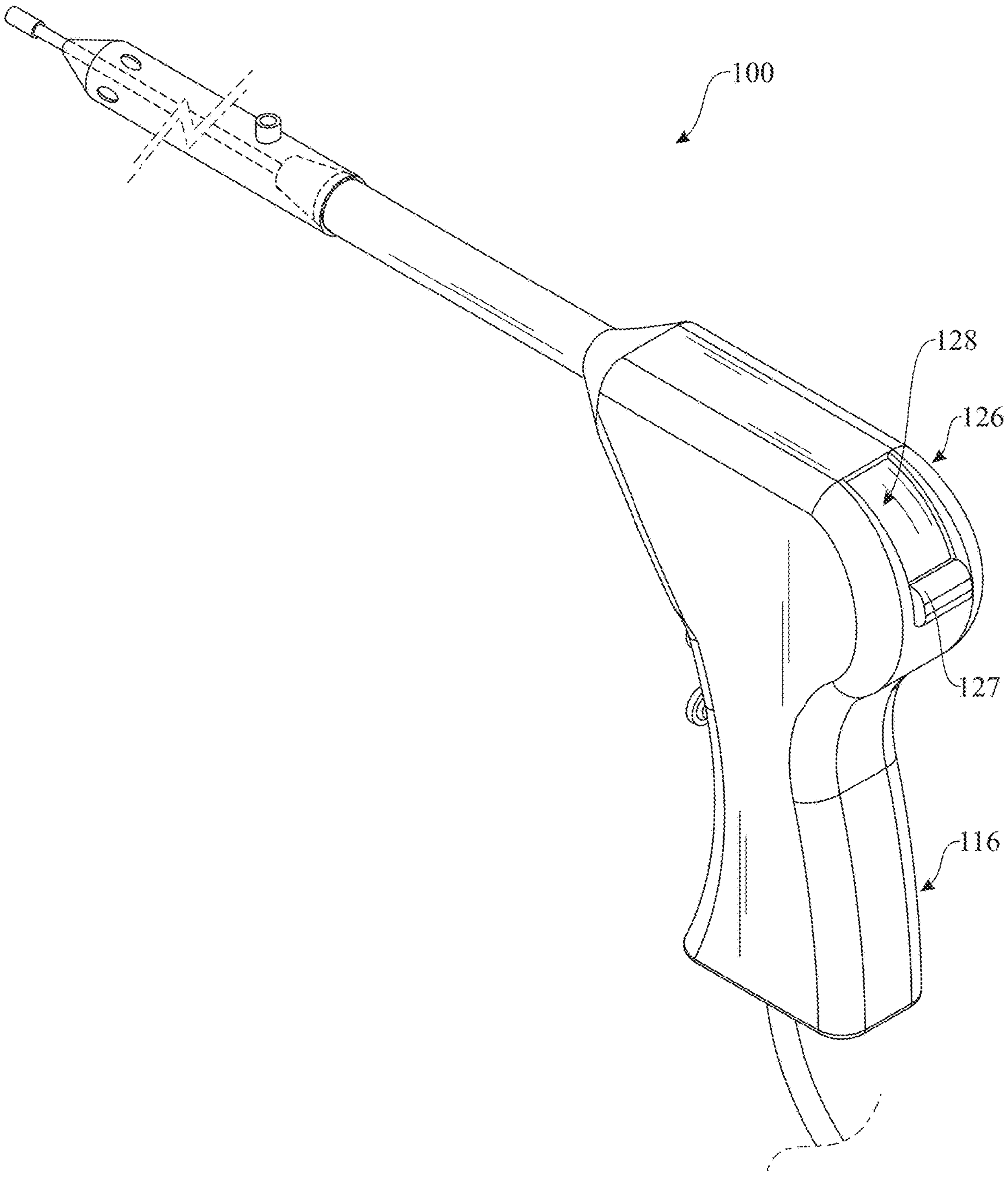
FIG. 2 presents a rear, side, upper perspective view showing the first embodiment of the urinary catheter placement device of the present invention, illustrating a mechanism to control the advance and retraction of the guide wire unit.
Figure 4:
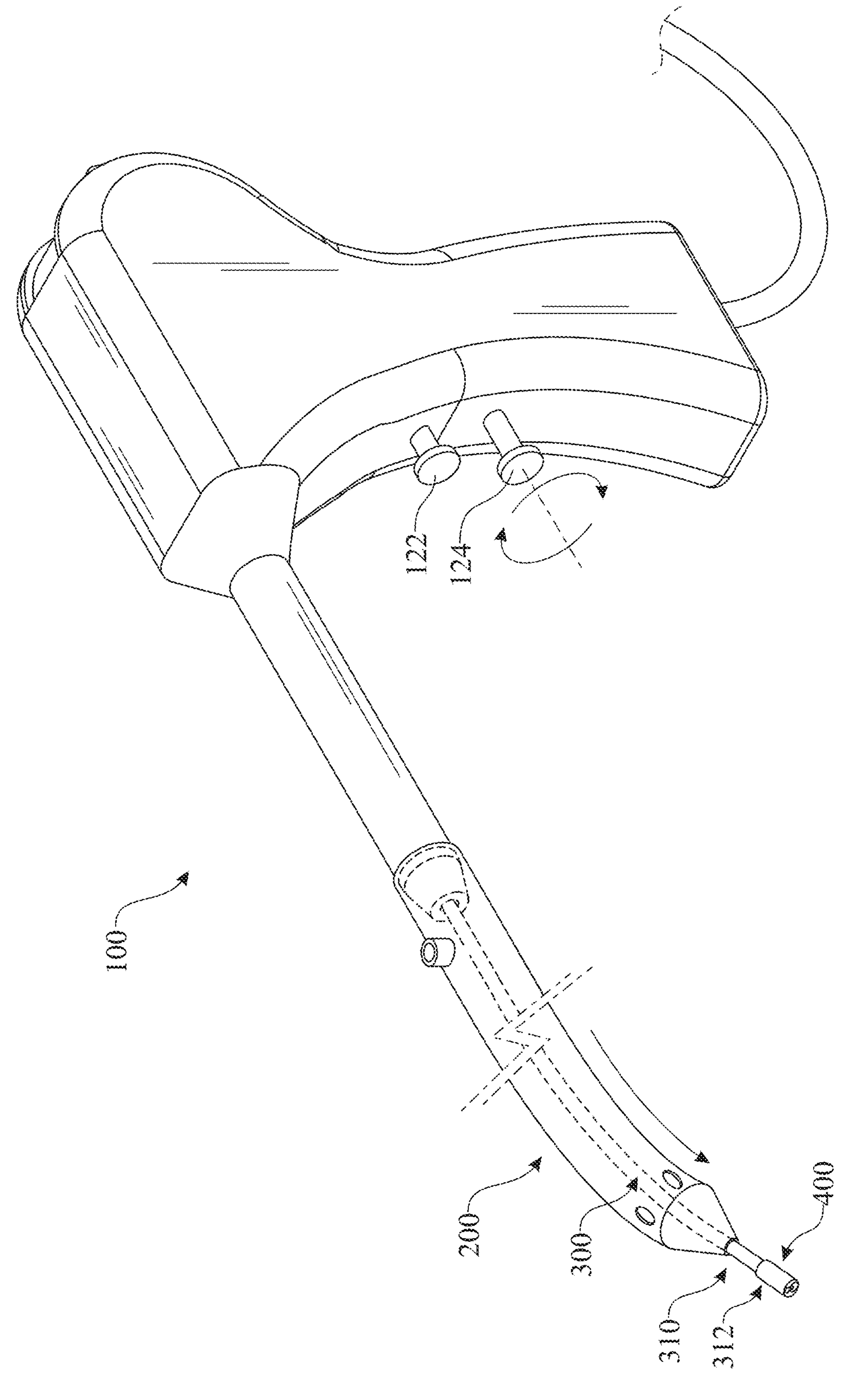
FIG. 4 presents a front, side, upper perspective view showing the first embodiment of the urinary catheter placement device of the present invention, illustrating user control of a steering operation for the combination guide wire and catheter.
Figure 5:
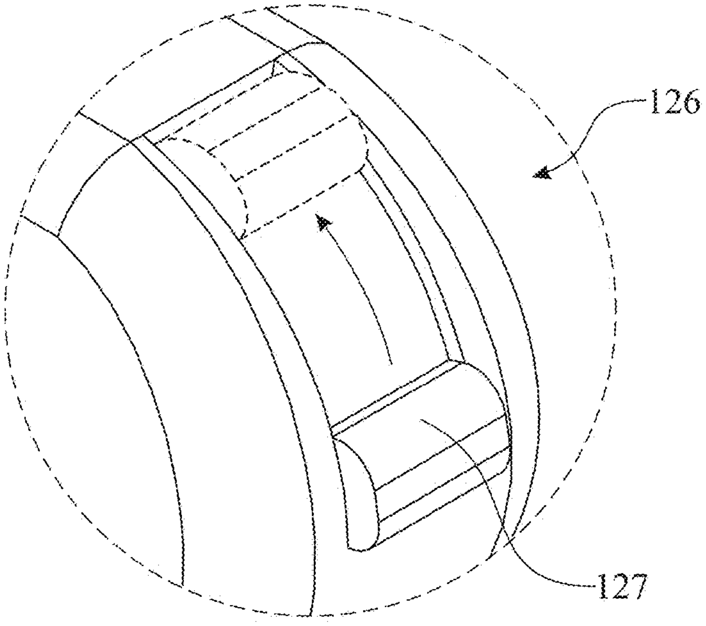
FIG. 5 presents an enlarged, sectional, perspective view of an adjustable switch mechanism of the first embodiment of the urinary catheter placement device of the present invention, illustrating how the switch mechanism is operated to control extension and retraction of the guide wire unit.
Figure 5A:
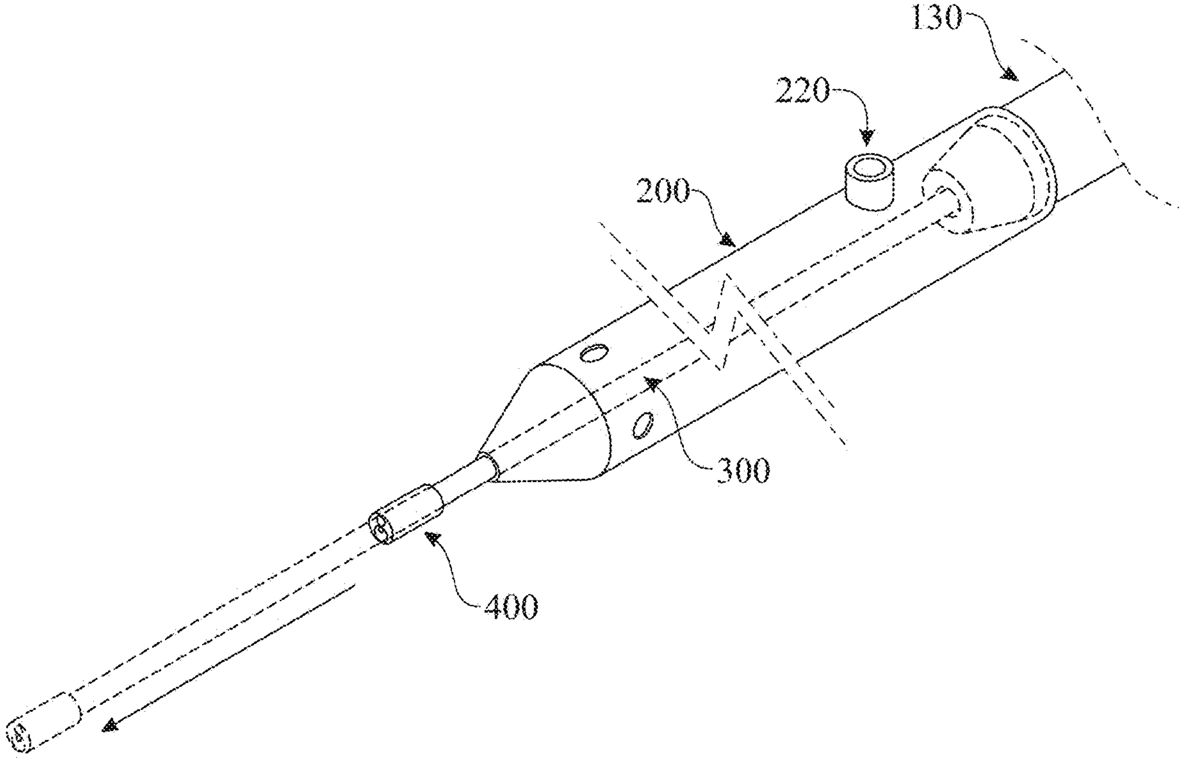
FIG. 5*a* presents an enlarged, sectional, front perspective view of the guide wire and catheter combination of the first embodiment of the urinary catheter placement device of the present invention, illustrating how the guide wire advances in response to operation of the switch mechanism disclosed in FIG. 5.

Referring now to FIGS. 2, 3-3*a*, 3*b*, 4, and 5-5*a*, the medical device 100 incorporates various user-activated and user-operated control features to manage and otherwise direct the various functionalities available with medical device 100. Referring first to FIGS. 2 and 5-5*a*, the medical device 100 includes a guide wire control mechanism generally illustrated at 126, which is configured to control the longitudinal movement of guide wire device 300. The mechanism 126 includes a switch 127 that moves from a lower position to a higher position along switch guide 128 (FIG. 5) to actuate the extension or advancement of the guide wire device 300 (FIG. 5*a*). In one exemplary form, the guide wire control mechanism 126 can be configured in a known way to offer variable speeds of advance/retract depending upon the location of switch 127 within guide 128. Prior to use, the guide wire device 300 is fully retracted within medical device 100. This condition would correspond to the lower position of switch 127. At the appropriate time requiring extension of guide wire device 300, the switch 127 is moved to the upper position, which actuates the advancing motion indicated in FIG. 5*a*. In particular, the guide wire device 300 advances through the bore of instrument barrel 130, traverses the lumen 214 of catheter 200, and then exits catheter 200 via the front opening 213 at the tip section 215 of the distal portion 212 of catheter 200 (FIG. 1). The extended guide wire device 300 can then be withdrawn or retracted at the appropriate time by moving the raised switch 127 back to its lower position. As mentioned previously, in its original wound condition, the guide wire device 300 is loaded into device 100 in a spooled or reeled arrangement. Any conventional means known to those skilled in the art can be used to provide the actuator for controlling the winding and unwinding of the guide wire device 300. The guide wire control mechanism 126 is conveniently located at the hammer area for the gun-style configuration of instrument body 110, making it easy for the operator holding device 100 to maneuver switch 127 with a thumb manipulation.

Referring now to FIG. 4, medical device 100 incorporates a feature to steer guide wire device 300. In particular, the trigger control mechanism 120 (FIG. 1) includes a user-operated control knob 124 that is configured to actuate a bending action at the distal portion 310 of guide wire device 300, specifically acting to maneuver or manipulate the tip section 312 (FIG. 1). The bending action is actuated in the guide wire mechanism located in the tip section 312, which effectuates an overall bending of the guide wire device 300 because of the integral bundling of the components within the insertion tube 302 of guide wire device 300 (FIG. 1). The bending action, in one form, involves a lateral redirection of the tip section 312 based on the circular orientation (e.g., turning angle) of rotary-type knob 124. As the knob 124 is rotated, the guide wire mechanism disposed at the tip section 312 is responsively and proportionally bent (i.e., deflected from the longitudinal axis of the straight, unbent configuration of guide wire device 300). In one exemplary embodiment, the knob 124 is configured to rotate and pivot (i.e., move to the right, left, up, down, or in any radial direction), similar to an analog stick, to move or otherwise bed the guide wire at the tip section 312. It is sufficient to just bend the tip section 312 in order to redirect the entire guide wire device 300, since the tip section 312 occupies a leading position and thus its deflection acts to steer the entire guide wire device 300. In one exemplary form, rotation of knob 124 in one direction (e.g., counterclockwise) will bend the tip section 312 to one side (e.g., left), while rotation in the other direction (e.g., clockwise) will bend the tip section 312 to the other side (e.g., right). Further rotation of knob 124 will increase the amount or degree of bending away from the central longitudinal axis. The knob 124 preferably has a 360-degree range, making it possible for the operator to bend the tip section 312 in any direction desirable. As shown, too, the bending of tip section 312 will correspondingly steer catheter 200, which follows the movement of guide wire device 300 in a tracking, guided fashion. Any conventional means known to those skilled in the art can be used to provide the actuator for controlling the bending of guide wire device 300.

The user is able to actuate a two-pronged movement of guide wire device 300. First, the user can direct a longitudinal movement of guide wire device 300 (advance and retract) via selective operation of switch 127 of guide wire control mechanism 126 (FIGS. 2, 5-5*a*). Second, the user can direct a bending or steering movement of guide wire device 300 via selective operation of knob 124 (FIG. 4), which actuates a bending action in tip section 312 of guide wire device 300.

Referring now to FIGS. 3-3*a* and 3*b*, medical device 100 incorporates a feature to actuate the dispersal of fluid at the tip section 312 of guide wire device 300, which is designed to apply cleaning fluid to the lenses of the video camera and light source combination 422. In particular, the trigger control mechanism on instrument body 110 (FIG. 1) includes a push-button trigger or switch 122 that controls the actuation of fluid discharge 430 from irrigation port 421 at the tip section 312 of guide wire device 300 (FIG. 3*a*). As shown, when a cleaning or irrigation operation is desired, the user presses trigger 122 (e.g., with index finger), which effectuates the discharge of fluid 430 from irrigation port 421 that is directed towards combination 422 for cleaning purposes. Any conventional means known to those skilled in the art can be used to provide the actuator for controlling the irrigation feature attending the activation of irrigation switch 122. In an alternative tip section design, the tip section 800 may include a conical tip with a substantially rounded outermost tip portion 819 (FIG. 3*b*). The tip section 800 may also include a viewing unit comprising a camera and light combination 422 and an irrigation line and outlet port 821. One will appreciate that the location of the camera, light source, and irrigation lumen are interchangeable in any configuration that would maximize the viewing and functionality of the device. Accordingly, the tip section may include other geometric shapes that will overall aid in the use of the medical device 100.

Figure 6:
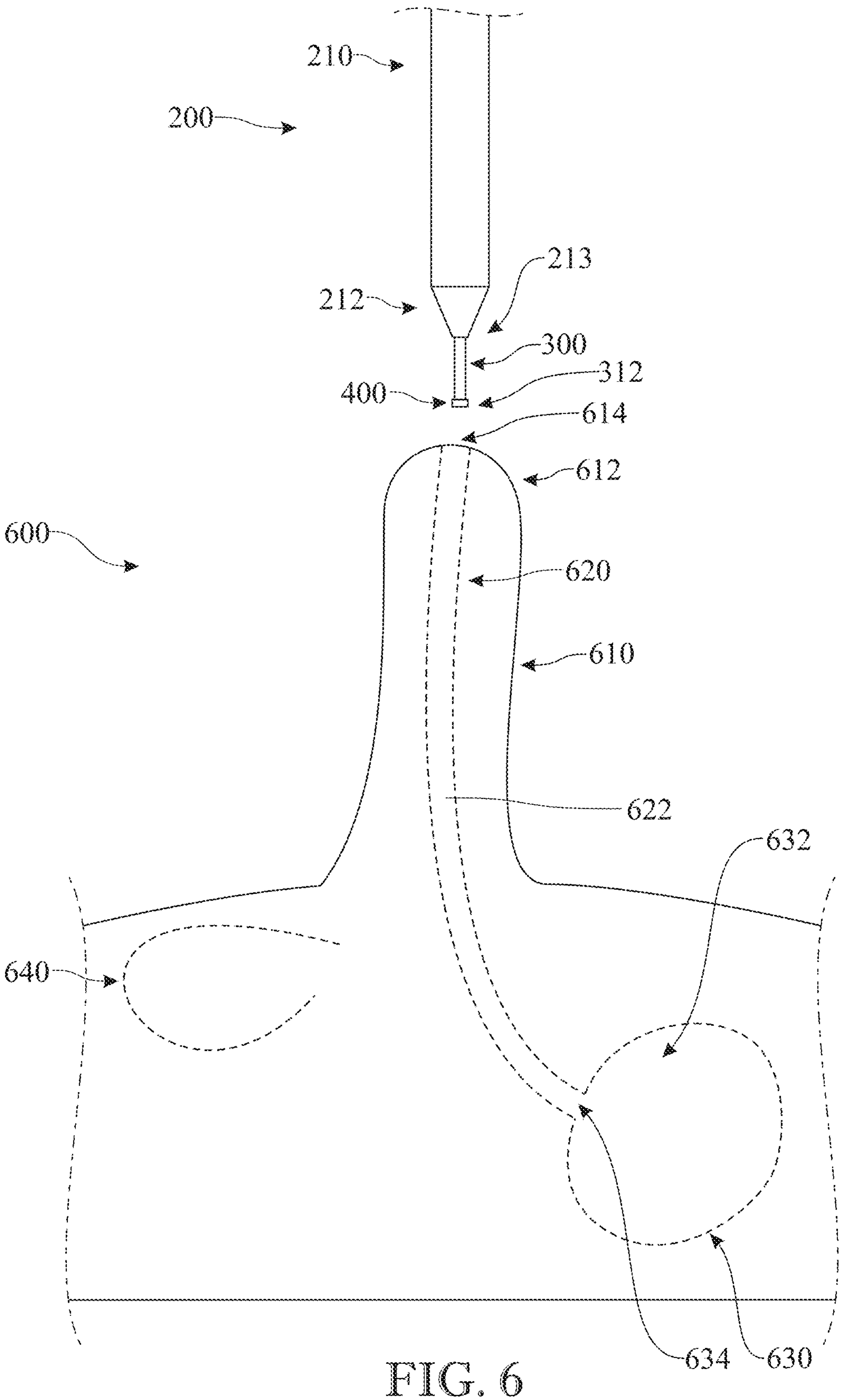
FIG. 6 is a partial, upper plan section view of the distal portion of the catheter and guide wire combination, and a partial, interior plan diagrammatic view of the male urogenital system, illustrating the preliminary positioning of the guide wire adjacent the urethral opening in accordance with a urethral catheterization and urine evacuation process.
Figure 7:
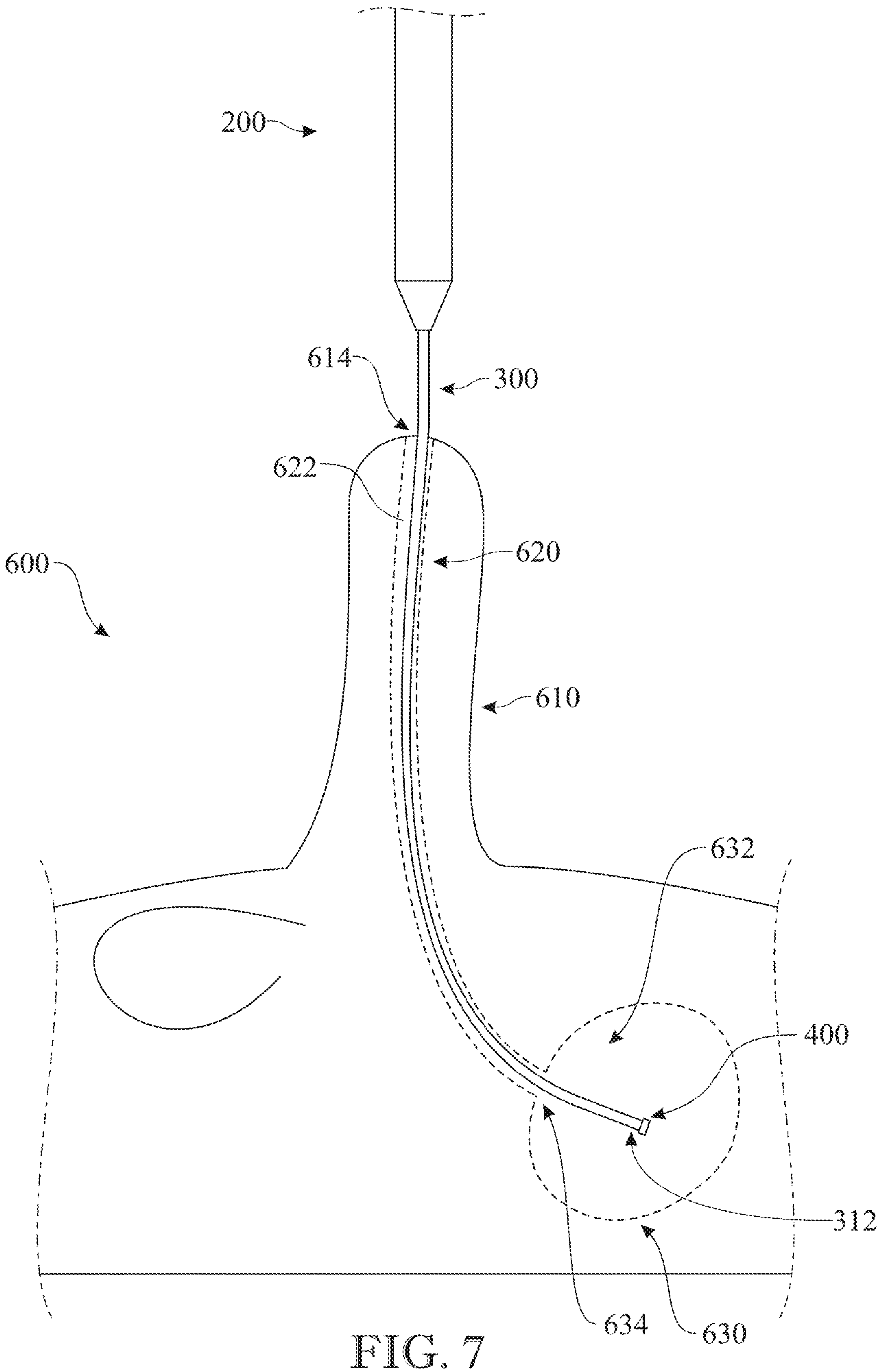
FIG. 7 shows a view similar to FIG. 6 and depicts a further step in the process, illustrating the routing of the guide wire through the urethra and into bladder.
Figure 8:
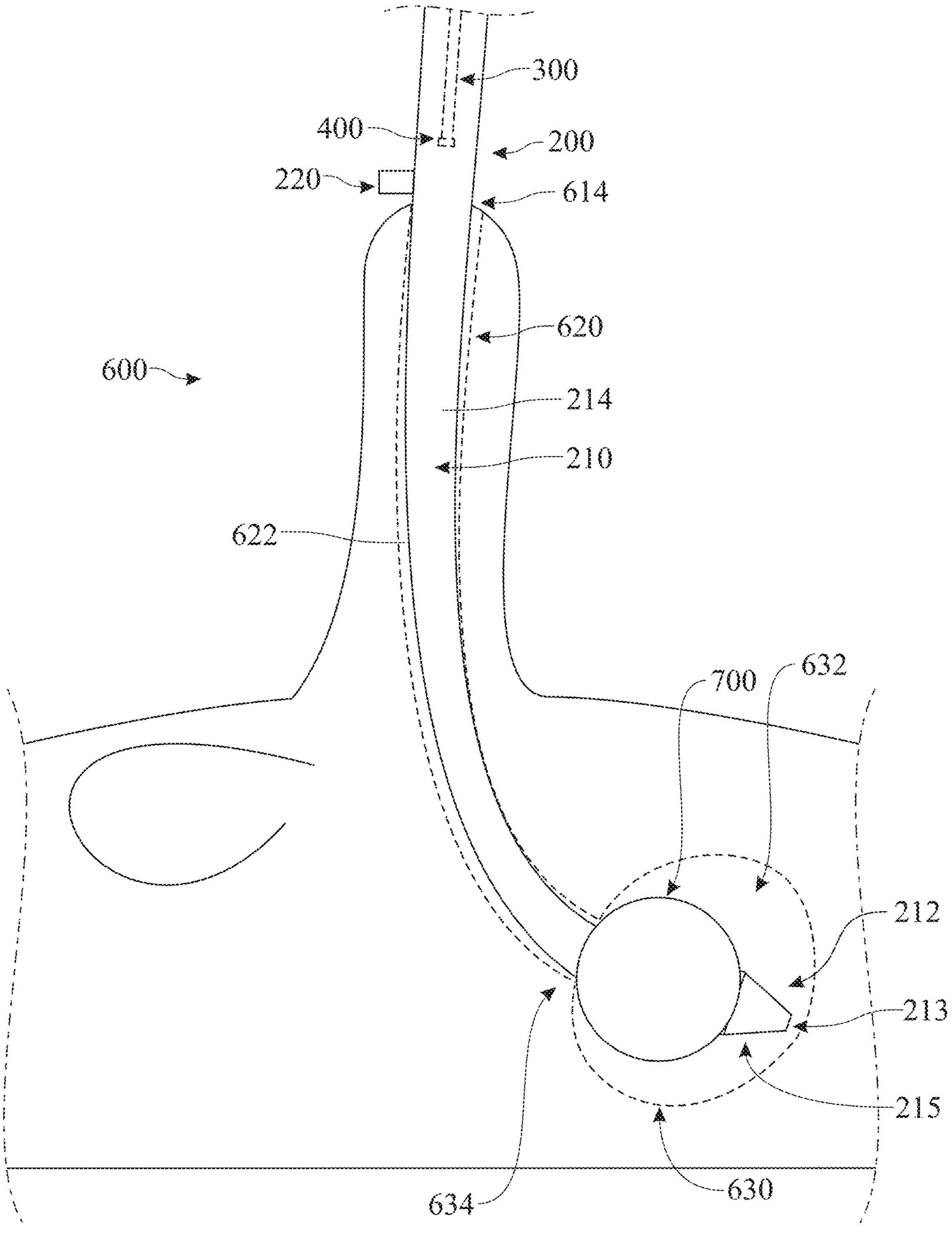
FIG. 8 shows a view similar to FIG. 7 and depicts a further step in the process, illustrating the guided insertion of the distal tip of the catheter into the bladder, withdrawal of the guide wire, and inflation of the dilator element to secure the catheter in place, operations preliminary to the urine evacuation step.

Referring now to FIGS. 6-8, an exemplary operation of medical device 100 is described. The medical device 100 is deployed in order to place catheter 200 into the patient bladder and evacuate urine from it. The anatomy of the patient includes the male urogenital system 600 having a penis 610, the head or glans 612 of penis 610, and the urethral meatus 614 (i.e., urethral opening or orifice at the tip of penis glans 612). The urethra generally illustrated at 620 includes the urethral duct or tube 622 that extends from the urethral opening 614 to bladder neck 634, which defines the threshold or transition into bladder 630. The bladder 630 defines an interior reservoir or urinary cavity 632 where urine collects from the kidney. For perspective, the scrotum or testicle 640 is also shown. Various medical indications require the intervention of a catheter to empty the bladder when normal urination cannot take place. For example, common causes of urinary retention include prostate enlargement and urethral stricture.

Referring first to FIG. 6, the medical device 100 is positioned so that the tip section 312 of guide wire device 300 is aligned with the urethral opening 614, typically in close, adjacent juxtaposed relationship. Prior to this, the operator advances guide wire device 300 so that it exits the front axial opening 213 at the terminus of the distal portion 212 of catheter 200. In this extended condition of guide wire device 300, the viewing unit 400 located at tip section 312 of guide wire device 300 defines the leading edge for insertion into urethra 620. The catheter 200 can be provided in any appropriate form suitable to the application. The catheter 200 is a separate component that can be installed on medical device 100 when the occasion arises for the deployment of medical device 100, namely, an intervention and treatment protocol to evacuate bladder 630. This installation involves placing the open-ended proximal portion 211 of catheter 200 over the distal portion 132 of barrel 130 of medical device 100 (FIG. 1). Of course, one will appreciate that certain embodiments will include an embodiment, where the open-ended proximal portion 211 of catheter 200 is preassembled over the distal portion 132 of barrel 130 of medical device 100.

Referring now to FIG. 7, the next step in the catheterization process involves the placement of the guide wire device 300 into the urinary tract, specifically to reach and enter the bladder 630 through the urethra 620. In particular, the operator continues to advance guide wire device 300, first inserting guide wire device 300 into the urethra 620 via the urethral opening 614. The passage of guide wire device 300 through urethra 620 continues until the tip section 312 of guide wire device 300 traverses the bladder neck 634 and enters the cavity 632 of bladder 630. This process of advancing guide wire device 300 through urethra 620 involves unreeling the coiled arrangement of guide wire device 300, which is packaged in a wound, bundled arrangement within medical device 100. At the same time that guide wire device 300 is being advanced through urethra 620, the user is simultaneously monitoring the travel and progress of guide wire device 300 and making any steering or navigational adjustments as needed. In particular, the user is simultaneously observing the video images acquired from the camera-equipped viewing unit 400 located at the tip section 312, which provides a live video feed of the urethral path immediately in front of and surrounding the leading edge of guide wire device 300. Based on what the operator is visualizing in terms of the interior cavity of urethra 620, the operator maneuvers the guide wire device 300 as appropriate to continue navigation through urethra 620. The operator continues to monitor the video feedback to make contemporaneous evaluations of the progress being made in the travel of the guide wire device 300 and to render determinations about how best to adjust the steering and maneuvering of guide wire device 300, if so needed.

The bending ability of the tip section 312 provides several distinct advantages. First, the viewing direction afforded by the camera-equipped viewing unit 400 is spatially comprehensive (omni-directional) since the video camera can be pointed in any direction, based on the ability to steer the tip section 312 and reorient its directionality. What this means is that the user is able to see the entire field within urethra 620 proximate tip section 312 and make informed decisions about how to navigate more difficult, complex, or tortuous paths. Second, if guide wire device 300 encounters difficult pathways within urethra 620, such as prostate-induced narrowing of the urethra (due to prostate enlargement), or urethra strictures (due to other causes), the user can successfully navigate these problem areas by carefully steering tip section 312 through them, a process that is augmented by the user being able to contemporaneously assess the navigational progress by analyzing the video feedback from the camera-equipped viewing unit 400. Additionally, the video feed helps the user to manage a safe and trauma-free guided navigation of guide wire device 300 through urethra 620 and into bladder 630, a task especially useful when negotiating any obstacles and steering through more confined spaces.

Referring now to FIGS. 7 and 8, the next step in the catheterization process involves the placement of the catheter 200 into the urinary tract, specifically to reach and enter the bladder 630 through the urethra 620, using the installed guide wire device 300 as the means to position catheter 200 and conduct its travel. In particular, once the guide wire device 300 is suitably extended into bladder 630 (FIG. 7), the catheter 200 is passed over guide wire device 300, a process in which catheter 200 tracks and follows the pathway established by guide wire device 300 in a guided course of travel. Similar to the passage of guide wire device 300, the catheter 200 enters the urethra 620 via urethral opening 614 (with catheter distal portion 212 leading the way), traverses along and through the length of urethra 620, and enters bladder 630 via bladder neck 634. Any means known to those skilled in the art can be used to advance catheter 200 along guide wire device 300. The medical device 100 includes an inflatable balloon 700 on the catheter 200 to help secure the catheter in the bladder. In one form, the dilator 700 is a balloon. Prior to its deployment, balloon 700 is carried by the catheter 200 in a deflated state. After guide wire device 300 is satisfactorily extended into bladder 630, which the operator is able to confirm and verify using the video images acquired from the camera-equipped tip section 312 of guide wire device 300, the operator advances the deflated balloon 700 into position at a suitable location along catheter 200. The balloon placement is appropriately made in order to ensure that when inflated, balloon 700 will be located in bladder 630 in a securing position.

Once the deflated balloon 700 is in place, it is inflated (as shown). For this purpose, catheter 200 is fitted with an inflation hub or port 220 (located upstream and accessible to the user), which is connected to a supply of pressurized air in a syringe. A pneumatic line (not shown) is provided that runs through catheter 200, extending from inflation hub 220 to balloon 700 and communicating the pressurized air. Both the inflation and deflation of the balloon 700 is done through the use of a syringe (not shown) The balloon 700 will typically occupy a position at a point somewhere rearward of the distal portion 212 of catheter 200. The manner of carrying balloon 700 in catheter 200, and advancing it into position where it is then inflated, can employ any suitable conventional means known to those skilled in the art. When balloon 700 is inflated, it functions as an anchor or securing means to stabilize the placement of catheter 200 in bladder 630 and ensure that catheter 200 (i.e., tip section 215 of distal portion 212) will not dislodge or dislocate from bladder 630. At this point, once catheter 200 is secured with the balloon 700, the guide wire device 300 can be fully withdrawn from the patient, simply reversing course through the extended (deployed) catheter 200 and returning to its original placement in medical device 100. The deployed catheter 200 remains in place, extending into bladder 630. The medical procedure can now proceed to the evacuation of urine from bladder 630 through the deployed catheter 200.

With continued reference to FIGS. 7 and 8, the medical device 100 of the present invention employs various features to manage and facilitate the evacuation of urine from bladder 630 through the deployed catheter 200. The passage of urine into catheter 200 can occur through several portals in catheter 200, which serve as drainage inlets to communicate urine from bladder 630 into the catheter lumen 214. One of these drainage inlets is the front opening 213 formed at the terminus of tip section 215 of distal portion 212 of catheter 200. Once the guide wire device 300 is withdrawn from the catheter lumen 214, this front opening 213 in the catheter tip section 215 becomes available as an open space through which urine can pass into catheter lumen 214. Other drainage inlets (not shown) can be provided on side surfaces of the catheter lumen 214, in a conventional manner well known to those skilled in the art. The urine that is withdrawn from bladder 630 through these drainage inlets (as provided in the distal portion 212 of catheter 200, i.e., tip section 215) is communicated through the catheter lumen 214 and flows towards the proximal portion 211 of catheter 200. Conventional means can be used to facilitate the reverse flow of urine through catheter 200, such as gravity-assisted mechanisms, and adaptations of medical device 100 to incorporate these means are will within the purview of one skilled in the art. At the proximal portion 211 of catheter 200, the evacuated urine flowing in lumen 214 is removed from catheter 200 and collected for disposal. Catheter 200 can be adapted to incorporate any suitable conventional means to facilitate such urine removal and collection. In one implementation, for example, a pluggable outlet port (not shown) can be provided at the proximal portion 211 of catheter 200 and disposed in fluid communication with lumen 214. During urine evacuation, this outlet port is unplugged and connected to an external collection receptacle to receive urine that flows out of catheter lumen 214 through this outlet port. According to one feature of the present invention, the interface or transition between the proximal portion 211 of catheter 200 and the distal portion 132 of barrel 130 of device 100 is adapted to provide a sealing function that prevents urine withdrawn through catheter lumen 214 from entering barrel 130 or leaking out of catheter lumen 214. This sealing function is needed since the terminus of catheter 200 at its proximal portion 211 is an open-ended formation. According to one aspect of the invention, distal portion 132 of barrel 130 is configured to incorporate a scalable plug that forms a fluid-tight engagement with the open-ended terminus of proximal portion 211 of catheter 200. During assembly, the catheter 200 (at proximal portion 211) is fit onto the barrel 130 of medical device 100 (at distal portion 132). In one implementation, for example, the distal portion 132 of barrel 130 is configured with a sealing structure at its terminus 133 that fully covers this terminus, except for a generally central aperture through which the guide wire device 300 can pass. This plug-like sealing structure provided at the distal end of barrel 130 functions as a leakage/drainage protector and a catheter plug.

The medical device 100 can be deployed in various ways to perform the bladder evacuation process, adapting or employing techniques known to those skilled in the art. In one illustrative procedure, for example, the urinary catheter can be placed over the guide-wire using a Seldinger-like technique.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A method for using a medical device to perform a bladder evacuation process, comprising the steps of:
- providing a medical device, comprising
  - an instrument body including a handle portion and a barrel portion with an opening,
  - an elongated tube including a lumen, an inflation port, and an inflatable balloon on a distal end of the elongated tube, wherein an end portion of the elongated tube engages the barrel portion of the instrument body,
  - a guide wire assembly carried by the instrument body, the guide wire assembly comprising an insertion tube configured to be selectively advanced and retracted along at least one path of travel including the barrel portion of the instrument body, the lumen of the elongated tube, and beyond the distal end of the elongated tube, and
  - at least one control switch configured to manipulate the insertion tube's movement;
- inserting the insertion tube into a urethral orifice toward a bladder;
- advancing the elongated tube into the urethral orifice, the elongated tube traveling over the insertion tube toward the bladder; and
- removing the insertion tube from the bladder,
  - wherein removal of the insertion tube allows fluid to evacuate from the bladder.

2. The method of claim 1, wherein the elongated tube is selectively anchored to surrounding bladder tissue by inflating the inflation balloon.

3. The method of claim 1, wherein the elongated tube includes a dilator configured to aid the advancement of the elongated tube over the insertion tube into the urethral orifice and toward the bladder.

4. The method of claim 1, the guide wire assembly further includes a video capturing camera disposed at a tip portion of the insertion tube.

5. The method of claim 1, wherein the guide wire assembly further includes an irrigation fluid dispensing port disposed at a tip portion of the insertion tube.

6. The method of claim 5, wherein the instrument body includes an interior compartment that retains a fluid reservoir for storing irrigation fluid that is dispensable at the tip portion of the insertion tube through the irrigation fluid dispensing port.

7. The method of claim 1, wherein the distal end portion of the elongated tube includes a tapered profile.

8. The method of claim 1, wherein the guide wire assembly further includes an illumination device disposed at a tip portion of the insertion tube.

9. The method of claim 1, wherein the elongated tube is removable.

10. The method claim 1, wherein the elongated tube includes at least one evacuation opening proximate to the distal end.

11. The method of claim 1, wherein the medical device includes at least a first control trigger disposed on a first portion of the instrument body configured to manipulate the insertion tube's movement.

12. The method of claim 11, wherein the medical device includes at least a second control trigger on a second portion of the instrument body configured to manipulate the insertion tube's rotational movement.

* * * * *